(12) United States Patent
Kubota et al.

(10) Patent No.: US 11,123,269 B2
(45) Date of Patent: Sep. 21, 2021

(54) TRANSPARENT SOLID COMPOSITION

(71) Applicant: SHISEIDO COMPANY, LTD., Tokyo (JP)

(72) Inventors: Shun Kubota, Kanagawa (JP); Hiroki Gomi, Osaka (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 0 days.

(21) Appl. No.: 16/320,507

(22) PCT Filed: Aug. 7, 2017

(86) PCT No.: PCT/JP2017/028555
§ 371 (c)(1),
(2) Date: Jan. 25, 2019

(87) PCT Pub. No.: WO2018/030326
PCT Pub. Date: Feb. 15, 2018

(65) Prior Publication Data
US 2020/0179241 A1 Jun. 11, 2020

(30) Foreign Application Priority Data
Aug. 8, 2016 (JP) .............................. JP2016-155402

(51) Int. Cl.
| | | |
|---|---|---|
| *A61K 8/02* | (2006.01) | |
| *A61K 8/31* | (2006.01) | |
| *A61K 8/35* | (2006.01) | |
| *A61K 8/36* | (2006.01) | |
| *A61K 8/37* | (2006.01) | |
| *A61K 8/41* | (2006.01) | |
| *A61K 8/49* | (2006.01) | |
| *A61K 8/88* | (2006.01) | |
| *A61K 8/92* | (2006.01) | |
| *A61Q 17/04* | (2006.01) | |

(52) U.S. Cl.
CPC ............ *A61K 8/0229* (2013.01); *A61K 8/022* (2013.01); *A61K 8/31* (2013.01); *A61K 8/35* (2013.01); *A61K 8/361* (2013.01); *A61K 8/37* (2013.01); *A61K 8/411* (2013.01); *A61K 8/4966* (2013.01); *A61K 8/88* (2013.01); *A61K 8/92* (2013.01); *A61Q 17/04* (2013.01); *A61K 2800/262* (2013.01)

(58) Field of Classification Search
CPC ........ A61Q 19/00; A61Q 15/00; A61Q 17/04; A61Q 1/04; A61Q 19/10; A61Q 1/02; A61Q 1/06; A61Q 1/10; A61Q 5/06; A61Q 19/04; A61Q 1/00; A61Q 1/08; A61Q 5/02; A61Q 3/02; A61Q 19/08; A61Q 1/12; A61Q 5/065; A61Q 5/10; A61Q 13/00; A61Q 5/12; A61Q 19/001; A61Q 5/04; A61Q 19/007; A61Q 5/00
See application file for complete search history.

(56) References Cited

FOREIGN PATENT DOCUMENTS

| | | | | |
|---|---|---|---|---|
| EP | 3409263 A1 | 12/2018 | | |
| EP | 3616679 A1 | 3/2020 | | |
| JP | H01163111 A | 6/1989 | | |
| JP | 2-180805 A | * 7/1990 | ............... | A61K 8/00 |
| JP | H02180805 A | 7/1990 | | |
| JP | H02264707 A | 10/1990 | | |
| JP | H0491010 A | 3/1992 | | |
| JP | H09235210 A | 9/1997 | | |
| JP | 2000204016 A | 7/2000 | | |
| JP | 2001-172128 A | 6/2001 | | |
| JP | 2003095848 A | 4/2003 | | |
| JP | 2005213145 A | 8/2005 | | |
| JP | 2007314459 | * 12/2007 | ............... | A61K 8/25 |
| JP | 2007314459 A | 12/2007 | | |
| JP | 2009114161 | * 5/2009 | ............... | A61K 8/02 |
| JP | 2009114161 A | 5/2009 | | |
| WO | 2018/198800 A1 | 11/2018 | | |

OTHER PUBLICATIONS

Kuniko et al., JP2-180805A, Jul. 13, 1990, translation of description. (Year: 1990).*
Isamu et al., JP2007-314459, Dec. 6, 2007, translation of description. (Year: 2007).*
Takeshi, JP2009-114161A, May 28, 2009, translation of description. (Year: 2009).*
International Search Report dated Dec. 12, 2017 filed in PCT/JP2017/028555.
International Search Opinion dated Dec. 12, 2017 filed in PCT/JP2017/028555; partial translation.
Extended European Search Report (EESR) dated Feb. 21, 2020 issued in the corresponding European Patent Application No. 17839397.1.
Japanese Office Action dated May 26, 2021 issued in the corresponding Japanese Patent Application No. 2018-533025 and its English translation.
Chinese Office Action dated Mar. 29, 2021 issued in the corresponding Chinese Patent Application No. 201780047789.8 and its English translation.

* cited by examiner

*Primary Examiner* — Audrea B Coniglio
(74) *Attorney, Agent, or Firm* — Rankin, Hill & Clark LLP

(57) ABSTRACT

To provide a transparent solid composition having a high ultraviolet ray blocking effect, as well as superior moldability and stability. A transparent solid composition includes: (a) 12-hydroxystearic acid in an amount within a range from 1 to 15% by mass; (b) an oil having a refractive index within a range from 1.5 to 1.7; (c) an oil having a refractive index of 1.3 or greater and less than 1.5; and (d) one type or two or more types of an ultraviolet ray absorbing agent in an amount within a range from 5 to 50% by mass. The refractive index of the transparent solid composition is within a range from 1.47 to 1.55.

20 Claims, 2 Drawing Sheets

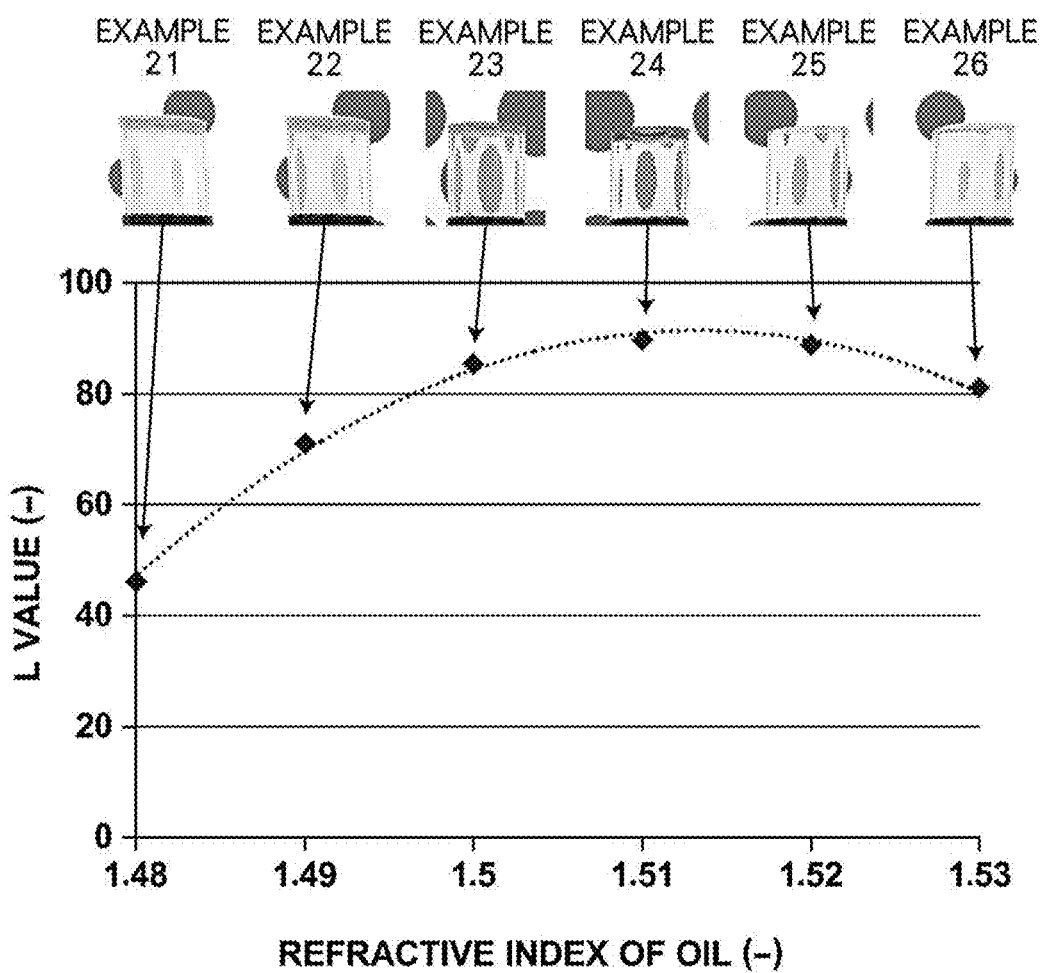

TRANSPARENT SOLID COMPOSITION

CROSS REFERENCE TO RELATED APPLICATIONS

The present application is a National Phase Entry of PCT International Application No. PCT/JP2017/028555 filed on Aug. 7, 2017, which claims priority under 35 U.S.C. § 119(a) to Japanese Patent Application No. 2016-155402 filed on Aug. 8, 2016. Each of the above applications is hereby expressly incorporated by reference, in its entirety, into the present application.

TECHNICAL FIELD

The present disclosure is related to a transparent solid composition which is transparent and has a high ultraviolet ray blocking effect, and a transparent solid cosmetic that contains the transparent solid composition as a base material.

BACKGROUND ART

Oil based transparent cosmetics have advantages principally in the attractiveness of their outer appearances, a finish having transparency when applied, etc. Therefore, various transparent base materials are being considered.

For example, Japanese Unexamined Patent Publication No. H1-163111 discloses a cosmetic that employs a transparent base material constituted by 12-hydroxystearic acid and an oil component, which has a refractive index within a range from 1.45 to 1.54. Further, Japanese Unexamined Patent Publication No. H2-264707 discloses a transparent solid cosmetic constituted by 2-hydroxystearic acid, heavy liquid paraffin, and an oil component in the form of a liquid. Japanese Unexamined Patent Publication No. H4-91010 discloses a transparent solid cosmetic that includes 12 hydroxystearic acid, a transparent oil component in the form of a liquid having a hydroxyl value of 120 or less, and methyl phenyl polysiloxane.

In addition, Japanese Unexamined Patent Publication No. H9-235210 discloses a transparent solid cosmetic, in which a dextrin fatty acid ester, heavy liquid paraffin, and an oil component in the form of a liquid are blended from the viewpoint of improving sheen when applied, as a transparent cosmetic in which a dextrin fatty acid ester is blended. Further, Japanese Unexamined Patent Publication No. 2005-213145 discloses a transparent solid composition, in which a dextrin fatty acid ester, a volatile oil, an oil having a refractive index within a range from 1.4 to 1.6, and a spherical powder having a refractive index within a range from 1.3 to 1.6 and an average particle diameter within a range from 3 μm to 30 μm are blended from the viewpoint of exhibiting a skin unevenness correcting effect to cause pores to become less conspicuous.

As described above, transparent cosmetics in which 12-hydroxystearic acid or a dextrin fatty acid ester are blended are widely known. However, if attempts to blend other effective components that exhibit additional operational effects to such transparent solid cosmetic are made, there were problems that moldability, stability, or transparency would deteriorate. These problems had been considered to be difficult to solve in preparations in which 12-hydroxystearic acid and dextrin fatty acids are blended as transparent solid components.

Japanese Unexamined Patent Publication No. 2007-314459 discloses a transparent solid composition for a transparent solid cosmetic which is thickened or gelled by an amino acid derivative modified silicone, in which a specific lysine derivative modified silicone, silicone oil, a polar oil having an IOB within a range from 0.17 to 0.63, and an ultraviolet ray absorbing agent are blended, from the viewpoint of maintaining a transparent outer appearance even when an ultraviolet ray absorbing agent, which does not dissolve easily in a non polar oil, is blended. However, there is a tendency for the stability of this transparent solid composition to deteriorate if the ultraviolet ray absorbing agent is blended in an amount exceeding 4% by mass, and the ultraviolet ray blocking effect thereof was not sufficient.

SUMMARY OF THE DISCLOSURE

Technical Problem

Expectations are growing for development of foundations, lip cosmetics, and cosmetic bases that exhibit a high ultraviolet ray blocking effect using a transparent base material that imparts an impression of natural skin. However, it had been difficult to achieve a sufficiently high ultraviolet ray blocking effect while maintaining moldability and stability in a transparent solid cosmetic with conventional techniques.

The present disclosure provides a transparent solid composition having transparency with an attractive outer appearance, has superior moldability and stability even if a significant amount of an ultraviolet ray absorbing agent is blended, and has a high ultraviolet ray blocking effect.

As a result of conducting intensive study in order to achieve such a transparent solid composition, the present inventors discovered that it is possible to produce a transparent solid composition having high transparency even if a significant amount of an ultraviolet ray absorbing agent is blended, and further has favorable moldability and superior stability, by blending 12-hydroxystearic acid, an oil having a refractive index within a range from 1.5 to 1.7, an oil having a refractive index of 1.3 or greater and less than 1.5, and an ultraviolet ray absorbing agent to obtain a refractive index from 1.47 to 1.55, to complete the present disclosure.

A transparent solid composition of the present disclosure includes: (a) 12-hydroxystearic acid in an amount within a range from 1 to 15% by mass, (b) an oil having a refractive index within a range from 1.5 to 1.7, (c) an oil having a refractive index of 1.3 or greater and less than 1.5, and (d) one type or two or more types of an ultraviolet ray absorbing agent in an amount within a range from 5 to 50% by mass, and is characterized by the refractive index of the transparent solid composition being within a range from 1.47 to 1.55. A high ultraviolet ray blocking effect can be achieved by including the ultraviolet ray absorbing agent in an amount within a range from 5 to 50% by mass. Therefore, a high ultraviolet ray blocking effect can be imparted, while a finish having transparency can be achieved when the transparent solid composition is applied.

The ultraviolet ray absorbing agent is not limited, but t-butyl methoxy dibenzoyl methane, ethylhexyl methoxy cinnamate, homomentyl salicylate (homosalate), octyl salicylate, octocrylene, 2-hydroxy 4-methoxybenzophenone, hexyl diethyl amino hydroxybenzoyl benzoate, bis ethylhexyl oxyphenol methoxy phenyl triazine, 2, 4, 6-tri-anilino-p-(carbo-2'-ethylhexyl-1'-oxy)-1, 3, 5-triazine etc., may be favorably employed.

The transparent solid composition of the present disclosure may further include a powder having a refractive index within a range from 1.45 to 1.55. By blending such a powder, stickiness can be suppressed and a smooth sensation of use can be imparted, while maintaining a transparent outer appearance.

In addition, it is preferable for the transparent solid composition of the present disclosure to include a volatile oil as the oil having a refractive index of 1.3 or greater and less than 1.5. By blending such a low refractive index volatile oil, oiliness can be reduced. Particularly, hydrocarbon series volatile oils have superior compatibility with 12-hydroxystearic acid, and can impart an even higher degree of transparency. Further, in the case that the volatile oil is included along with the aforementioned powder, the transparent solid composition will have a transparent outer appearance prior to application, but the volatile oil will evaporate when applied to the skin, the refractive indices of the powder and the oil will shift such that the composition will become semitransparent, and a skin unevenness correcting effect can be imparted.

The transparent solid composition of the present disclosure may be filled in a container or molded into any format, such as in the form of a stick, etc. By molding the transparent solid composition into the form of a stick, it will not be necessary to use any tools during application. In addition, application will be facilitated without a user's hands becoming dirty.

Further, the present disclosure provides a transparent solid cosmetic that includes the transparent solid composition as a base material.

Effects of the Disclosure

The transparent solid composition of the present disclosure has a high degree of transparency and stability even though it includes a significant amount of an ultraviolet ray absorbing agent. This transparent solid composition has a transparent outer appearance, and is capable of imparting an impression of natural skin when applied, while having superior moldability and stability, and further exhibits a high ultraviolet ray blocking effect.

BRIEF DESCRIPTION OF THE DRAWINGS

FIG. 2 A graph that shows the results of evaluations of L values employing a color difference meter for Examples 21 through 26 to be described later.

DESCRIPTION OF EMBODIMENTS

<(a) 12-Hydroxystearic Acid>

Figure 1:
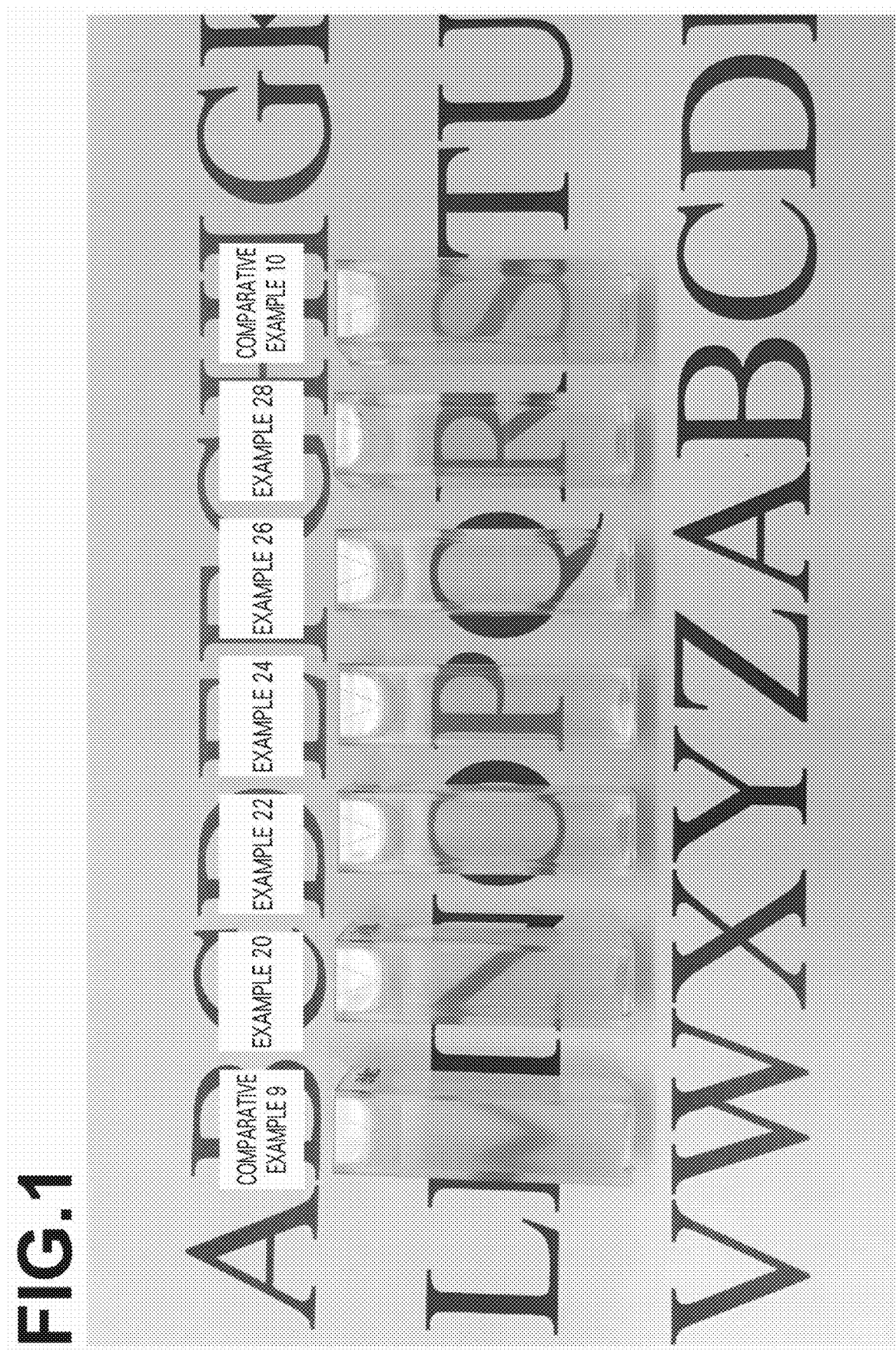
FIG. 1 A photograph of transparency evaluation.

12-hydroxystearic acid which is employed in the present disclosure is a hydrogenated ricinoleic acid, which is a saturated fatty acid having an asymmetric hydroxyl group at carbon at the 12 position, and is produced by hydrolyzing hydrogenated castor oil obtained by hydrogenating castor oil. It can also be obtained by hydrogenating a castor oil fatty acid obtained by hydrolysis of castor oil. A commercially available product may be utilized in the present disclosure.

The amount of 12-hydroxystearic acid which is included in a blend differs according to the format and use of an intended transparent solid cosmetic. However, the amount is generally within a range from 1 to 15% by mass, preferably within a range from 1 to 10% by mass, and more preferably within a range from 2 to 8% by mass in the transparent solid composition. If the amount of 12-hydroxystearic acid is less than 1% by mass, there are cases in which a sufficient hardness cannot be obtained, and if the 12-hydroxystearic acid is blended in an amount exceeding 15% by mass, transparency will deteriorate, which is not preferable.

<(b) Oil having a Refractive Index from 1.5 to 1.7>

Component (b) is an oil having a relatively high refractive index, with a refractive index within a range from 1.5 to 1.7 at a temperature of 25° C. Such a high refractive index oil is not limited, and examples include hydrogenated polyisobutane, trimethyl pentaphenyl polysiloxane, diphenyl dimethicone, and the like. For example, PH-1555HRIC [refractive index: 1.58] by Toray/Dow Corning, Silicone KF56 [refractive index: 1.5] by Shin Etsu Chemical Industries, and FZ-3156 [refractive index: 1.575] by Nippon Unicar are commercially available as trimethyl pentaphenyl polysiloxanes, and KF-54 [refractive index: 1.505] by Shin Etsu Chemical Industries, etc. are commercially available as diphenyl dimethicones. These products may be favorably utilized.

The amount of the high refractive index oil having a refractive index within a range from 1.5 to 1.7 to be blended in the transparent solid composition of the present disclosure is that which causes the average refractive index of all of the oil to be within a range from 1.47 to 1.55 in combination with a low refractive index oil. Therefore, the amount of the high refractive index oil is not particularly limited and will differ depending on the types and combinations of the high refractive index oil to be blended. However, it is preferable for the amount of the high refractive index oil to be blended to be within a range from 5 to 50% by mass, more preferably within a range from 10 to 40% by mass, and still more preferably from 15 to 35% by mass with respect to the amount of the composition.

<(c) Oil having a Refractive Index of 1.3 or Greater and Less than 1.5>

Component (c) is an oil component having a relatively low refractive index with a refractive index of 1.3 or greater and less than 1.5 at a temperature of 25° C. Examples of such low refractive index oils include, but are not limited to, for example, triethylhexanoin (refractive index: 1.45), tri (caprylic/capric acid) glyceryl (refractive index: 1.45), tri 2-ethylhexanoic acid glyceryl (refractive index: approximately 1.44), cetyl 2-ethylhexanoate (refractive index: approximately 1.44), trimethylolpropane trioctanoate (refractive index: approximately 1.45), squalane (refractive index: approximately 1.45), α-olefin oligomer (refractive index: approximately 1.46), glyceryl diisostearate (refractive index: approximately 1.46), diisostearyl malate (refractive index: approximately 1.46), polyglyceryl triisostearate (refractive index: approximately 1.47), macadamia nut oil (refractive index: approximately 1.47), liquid paraffin (refractive index: approximately 1.47), isododecane (refractive index: 1.42), isohexadecane (refractive index 1.43), light isoparaffin (refractive index: approximately 1.43), dimethyl polysiloxane (refractive index: approximately 1.40), polyoxy alkylene polyalkyl siloxane (alkylene=ethylene; refractive index: approximately 1.42), etc. Particularly, triethylhexanoin, tri (caprylic/capric acid) glyceryl, etc. may be favorably utilized.

In addition, although not limited, it is preferable for component (c) to include a volatile oil having a boiling point of 300° C. or less at normal pressure. By including a volatile oil, oiliness will be reduced, and the cosmetic finish will have little stickiness.

Such a volatile oil is not particularly limited, but from the viewpoint of compatibility with 12-hydroxystearic acid (component (a)), it is preferable to employ a hydrocarbon series volatile oil. Such a hydrocarbon series volatile oil having a refractive index of 1.3 or greater and less than 1.5 at a temperature of 25° C. is not limited: However, isododecane, isohexadecane, light isoparaffin, etc. may be favorably employed in the present disclosure. These oils have superior compatibility with 12-hydroxystearic acid (component (a)), and a solid composition with a higher transparency can be produced. The transparent solid composition of the present disclosure may contain no silicone type volatile oil. If a silicone type volatile oil is included, the transparency may deteriorate.

The amount of the low refractive index oil having a refractive index of 1.3 or greater and less than 1.5 to be blended in the transparent solid composition of the present disclosure is that which causes the average refractive index of all of the oil to be within a range from 1.47 to 1.55 in combination with the aforementioned refractive index oil. Therefore, the amount of the low refractive index oil is not particularly limited and will differ depending on the types and combinations of the low refractive index oil to be blended. However, it is preferable for the amount of the low refractive index oil to be blended to be within a range from 5 to 50% by mass, more preferably within a range from 10 to 40% by mass, and still more preferably from 15 to 35% by mass with respect to the amount of the composition.

The total amount of oil, which is obtained by mixing the high refractive index oil (component (b)) and the low refractive index oil (component (c)) to be blended is not particularly limited. However, it is preferable for the total amount of oil to be within a range from 10 to 80% by mass, and more preferably within a range from 20 to 70% by mass. If the amount of the oils is less than 10% by mass, it may be difficult to impart a finish with sheen to the solid composition. Meanwhile, if the oils are blended at a total amount greater than 80% by mass, there are cases in which stickiness is generated. Components (b) and (c) are blended such that the average refractive index of all of the oil is within a range from 1.47 to 1.55.

<(d) Ultraviolet Ray Absorbing Agent>

The ultraviolet ray absorbing agent which is employed in the present disclosure is selected from those that can be blended in external skin preparations such as cosmetics, etc., and is not particularly limited. Specific examples thereof include t-butyl methoxy dibenzoyl methane, ethylhexyl methoxy cinnamate (octyl methoxy cinnamate), phenyl salicylate, octyl salicylate, homomentyl salicylate (homosalate), ethylhexyl salicylate, octocrylene, 2-hydroxy 4-methoxy benzophenone, polysilicon-15, ethylhexyl triazone, hexyl diethyl amino hydroxybenzoyl benzoate, bis ethylhexyl oxyphenol methoxy phenyl triazine, oxybenzone-3, methylene bis benzotriazolyl tetramethyl butyl phenol, phenyl benzimidazole sulfonic acid, 2, 4, 6-trianilino-p-(carbo-2'-ethylhexyl-1'-oxy-1, 3, 5-triazine, {2-[4-(diethyl amino)-2-hydroxybenzoyl]} benzoate hexyl ester, 2, 4-bis-[{4-(2-ethylhexyloxy)-2-hydroxy}-phenyl]-6-(4-methoxy phenyl)-1, 3, 5-triazine, etc.

Particularly, t-butyl methoxy dibenzoyl methane, ethylhexyl methoxy cinnamate, homomentyl salicylate, octyl salicylate, octocrylene, 2-hydroxy 4-methoxy benzophenone, hexyl diethyl amino hydroxybenzoyl benzoate, bis ethylhexyl oxyphenol methoxy phenyl triazine, 2, 4, 6-trianilino-p-(carbo-2'-ethylhexyl-1'-oxy)-1, 3, 5-triazine, etc. may be favorably employed in the composition of the present disclosure.

One type or a combination of two or more types of the ultraviolet ray absorbing agents described above are blended such that the average refractive index of the ultraviolet ray absorbing agent is within a range from 1.47 to 1.55.

The amount of the ultraviolet ray absorbing agent which is blended is within a range from 5 to 50% by mass, and preferably within a range from 5 to 35% by mass with respect to the total amount of the composition. Blending a large amount of the ultraviolet ray absorbing agent is one of the characteristic features of the present disclosure.

Note that it is preferable for the transparent solid composition to not include a scattering agent. Cloudiness will be generated if a scattering agent is blended, and there are cases in which the degree of transparency will decrease, which is not preferable.

<Powder having Refractive Index from 1.45 to 1.55>

It is favorable for the transparent solid composition of the present disclosure to further include a powder having a refractive index within a range from 1.45 to 1.55 in addition to the indispensable components described above. If the refractive index of the powder is within the above range, the difference in refractive index from the oil component which is employed in the present disclosure will be small, and a high transparency can be realized in the base material. Such a powder is not limited, but may be, for example, (HDI/trimethyrolhexyl lactone) cross polymer (refractive index: approximately 1.5), nylon (refractive index: approximately 1.53), polyethylene (refractive index: approximately 1.51), polyurethane (refractive index: approximately 1.50), silicate anhydride (refractive index: approximately 1.45 to 1.50), etc. In addition, these powders may undergo a surface treatment such as a hydrophobizing process, etc. by a conventional method, and then blended.

The amount of such a powder to be blended is within a range from 15 to 60% by mass, and preferably within a range from 25 to 50% by mass with respect to the total amount of the composition. By matching the refractive indices of the oil and the powder, the composition can reduce stickiness and improve utility while maintaining a high degree of transparency. Further, in the case that the volatile oil is included along with such a powder, the transparent solid composition will have a transparent outer appearance prior to application, but the volatile oil will evaporate when applied to the skin, the refractive indices of the powder and the oil will shift such that the composition will become semitransparent, and a skin unevenness correcting effect can be imparted.

The present disclosure is directed to a transparent oil based solid composition or a transparent oil based solid cosmetic having the transparent oil based solid composition as a base material. Because the composition or the cosmetic is transparent and oil based, brightness, sheen, and a moisturizing sensation are imparted when applied, and skin can be made to appear plump.

In the present disclosure, the components described above are employed to prepare the transparent solid composition to have a refractive index within a range from 1.47 to 1.55. Within such a range of refractive indices, a transparent composition can be prepared. In particular, the composition will have an even higher transparency particularly in the case that the refractive index is within a range from 1.49 to 1.53, and therefore such a range is preferable.

Note that in the present disclosure, refractive indices are values measured by an AUTOMATIC REFRACTOMETER by Rudolph Research Analytical at a temperature of 25° C. With respect to powders, documented values are referred to.

The solid composition of the present disclosure refers to a composition which does not have fluidity at normal temperature (15° C. to 25° C.) and under normal pressure. The form of a stick, the form of a plate, the form of a balm, etc. are possible as the form of a preparation. Particularly, a preparation in the form of a stick does not require use of a finger or a tool and enables direct application to the skin, which facilitates use. Further, a transparent stick is attractive in appearance, and is also preferable because the transparency of the finish can be understood simply by viewing it.

In addition, the transparency of the transparent solid composition of the present disclosure may be evaluated by a measurement method to be described later, in which samples are poured into transparent resin containers such that the thicknesses thereof became 10 mm, and evaluating the visibility and the clarity of text placed under the containers written in Times New Roman font with a font size of 88, at a temperature of 25° C.

Note that it is preferable for the transparent solid composition of the present disclosure to further include an oil solidifying agent selected from the group consisting of dibutyl lauroyl glutamide, dibutyl ethylhexanoyl glutamide, polyamide-3, and polyamide-8, from the viewpoint that each of these are oil gelling agents that can provide a transparent solid object.

Arbitrary components may be blended in the transparent solid composition in addition to the indispensable components described above, as long as the effects of the present disclosure are not inhibited. Components which are generally blended into cosmetics may be added, and any transparent solid cosmetic may be produced by a conventional method.

The arbitrary components may be an oil, a higher alcohol, a higher fatty acid, a POE.POP dimethyl ether, a powder component, a surfactant, a humectant agent, a metal sequestering agent, an antioxidant agent, an oil soluble medicament, etc.

An animal/vegetable fat may be, for example, cocoa butter, coconut oil, hardened coconut oil, palm oil, palm kernel oil, wolfberry kernel oil, hardened oil, wolfberry wax, hydrogenated castor oil, etc.

A wax may be, for example, beeswax, candelilla wax, cotton wax, carnauba wax, bayberry wax, insect wax, spermaceti, montan wax, nucca wax, lanolin, kapok wax, lanolin acetate, liquid lanolin, sugarcane wax, isopropyl lanolin fatty acid, hexyl laurate, reduced lanolin, Burrow, hard lanolin, shellac wax, POE lanolin alcohol ether, POE lanolin alcohol acetate, POE cholesterol ether, lanolin fatty acid polyethylene glycol, POE hydrogenated lanolin alcohol ether, ceresin, micro crystalline wax, etc.

A hydrocarbon oil may be, for example, liquid paraffin, ozokerite, squalene, pristane, paraffin, petrolatum, etc.

The higher fatty acid is a fatty acid having alkyl groups with carbon numbers within a range from 9 to 30. The higher fatty acid may be capric acid, lauric acid, myristic acid, palmitic acid, stearic acid, arachic acid, behenic acid, melissic acid, etc. The alkyl groups may be branched, and also may have a substituent group such as an unsaturated bond, a hydroxyl group, a carboxyl group, a phenyl group, etc. The higher fatty acids may be unsaturated fatty acids such as palmitoleic acid, oleic acid, linoleic acid, linolenic acid, petroselinic acid, elaidic acid, ricinolic acid, lino elaidic acid, arachidonic acid, etc.; branched fatty acids such as isostearic acid; hydroxy carbonic acids such as 12-hydroxystearic acid, etc.

The higher alcohol is a higher alcohol having alkyl groups with carbon numbers within a range from 6 to 20. The higher alcohol may be caproyl alcohol, capryl alcohol, lauryl alcohol, myristyl alcohol, cetyl alcohol, stearyl alcohol, arachinyl alcohol, etc. The alkyl groups may be branched and may have a substituent group such as an unsaturated bond, a hydroxyl group, a carboxyl group, a phenyl group, etc.

The POE.POP dimethyl ether may be the alkylene oxide derivative disclosed in Japanese Unexamined Patent Publication No. 2003-113023, or the like.

The powder component may be, for example, an inorganic powder (for example, talc, kaolin, mica, sericite, muscovite, phlogopite, synthetic mica, red mica, biotite, vermiculite, magnesium carbonate, calcium carbonate, aluminum silicate, barium silicate, calcium silicate, magnesium silicate, strontium silicate, tungstenate metal salt, magnesium, silica, zeolite, barium sulfate, calcined calcium sulfate (baked gypsum), calcium phosphate, fluorine apatite, hydroxy apatite, ceramic powder, metal soap (for example, zinc myristate, calcium palmitate, and aluminum stearate), boron nitride, etc.); an inorganic white pigment (for example, titanium dioxide, zinc oxide, etc.); an inorganic red type pigment (for example, iron oxide, iron titanate, etc.); an inorganic brown type pigment (for example, γ-iron oxide, etc.); an Inorganic yellow pigment (for example, yellow iron oxide, ocher, etc.; an inorganic black type pigment (for example, black iron oxide, low order titanium oxide, etc.); an inorganic purple type pigment (for example, manganese violet, cobalt violet, etc.); an inorganic green pigment (for example, chromium oxide, chromium hydroxide, cobalt titanate, etc.); an inorganic blue type pigment (for example, ultramarine, Prussian blue, etc.); a pearl pigment (for example, titanium oxide coated mica, titanium oxide coated bismuth oxychloride, titanium oxide coated talc, colored titanium oxide coated mica, bismuth oxychloride, fish scale foil, etc.); a metal powder pigment (for example, aluminum powder, copper powder, etc.); an organic pigment such as zirconium, barium, and aluminum flakes (for example, organic pigments such as red number 201, red number 202, red number 204, red number 205, red number 220, red number 226, red number 228, red number 405, orange number 203, orange number 204, yellow number 205, yellow number 401, and blue number 404, red number 3, red number 104, red number 106, red number 227, red number 230, red number 401, red number 505, orange number 205, yellow number 4, yellow number 5, yellow number 202, yellow number 203, green number 3, and blue number 1); natural color (for example, chlorophyll, β-carotene, etc.); etc.

It is possible to blend the powder component described above in the transparent solid cosmetic of the present disclosure within a range that maintains the transparency of the cosmetic.

The lipophilic nonionic surfactant, may be, for example, a sorbitan fatty acid ester (for example, sorbitan monooleate, sorbitan monoisostearate, sorbitan monolaurate, sorbitan monopalmitate, sorbitan monostearate, sorbitan sesquioleate, sorbitan trioleate, diglycerol penta-2-ethylhexylate sorbitan, tetra-2-ethylhexyl acid diglycerol sorbitan, etc.); a glycerin polyglycerol fatty acid (for example, mono cottonseed oil fatty acid glycerin, glyceryl monoerucate, glycerin sesquioleate, glycerin monostearate, glycerin α,α'-oleate pyroglutamate, glycerin monostearate malate, etc.); a propylene glycol fatty acid ester (for example, propylene glycol monostearate, etc.); a hydrogenated castor oil derivative; glycerin alkyl ether; etc.

The hydrophilic nonionic surfactant may be, for example, a POE-sorbitan fatty acid ester (for example, POE-sorbitan monooleate, POE-sorbitan monostearate, POE-sorbitan monooleate, POE-sorbitan tetraoleate, etc.); a POE sorbit fatty acid ester (for example, POE-sorbitol monolaurate, POE-sorbit monooleate, POE-sorbitol pentaoleate, POE-sorbit monostearate, etc.); a POE-glycerin fatty acid esters (for example, a POE-monooleate such as POE-glycerin monostearate, POE-glycerin monoisostearate, POE-glycerin triisostearate, etc.); a POE-fatty acid ester (for example, POE-distearate, POE-mono dioleate, ethylene distearate, etc.); a POE-alkyl ether (for example, POE-lauryl ether, POE-oleyl ether, POE-stearyl ether, POE-behenyl ether, POE-2-octyldodecyl ether, POE-cholestanol ether, etc.); a POE.POP-alkyl ether (for example, POE.POP-cetyl ether, POE.POP-2-decyl tetradecyl ether, POE.POP-monobutyl ether, POE.POP-hydrogenated lanolin, POE.POP-glycerin ether, etc.); a POE-castor oil hardened castor oil derivative (for example, POE-castor oil, POE-hydrogenated castor oil, POE-hydrogenated castor oil monoisostearate, POE-hydrogenated castor oil triisostearate, POE-hydrogenated castor oil monopyroglutamic acid monoisostearic acid diester, POE-hydrogenated castor oil maleic acid, etc.); a POE-beeswax/lanolin derivative (for example, POE-sorbitol beeswax, etc.); an alkanol amide (for example, coconut oil fatty acid diethanolamide, lauric acid monoethanol amide, fatty acid isopropanol amide, etc.); a POE-propylene glycol fatty acid ester; a POE-alkyl amine; a POE-fatty acid amide; a sucrose fatty acid ester; trioleyl phosphate, etc.

The humectant agent may be, for example, polyethylene glycol, propylene glycol, glycerin, 1,3-butylene glycol, xylitol, sorbitol, maltitol, chondroitin sulfate, hyaluronic acid, mucoitin sulfate, caloninic acid, atelocollagen, cholesteryl-12-hydroxystearate, sodium lactate, bile salt, d, 1-pyrrolidone carboxylate salt, short chain soluble collagen, diglycerin (EO) PO adduct, isabiida extract, bupleurum extract, merylort extract, trehalose, erythritol, POE.POP random copolymer methyl ether, etc.

The metal ion sequestering agent may be, for example, 1-hydroxy ethane-1, 1-diphosphate, 1-hydroxy ethane-1, 1-diphosphonic acid tetrasodium salt, disodium edetate, trisodium edetate, tetrasodium edetate, sodium citrate, sodium polyphosphate, sodium metaphosphate, gluconic acid, phosphate, citric acid, ascorbic acid, succinic acid, edetic acid, trisodium ethylene diamine hydroxyethyl triacetate, etc.

The vitamin may be, for example, vitamin A, B1, B2, B6, C, E, derivatives thereof, pantothenic acid and derivatives thereof, biotin, etc.

The antioxidant agent may be, for example, a tocopherol, dibutyl hydroxyl toluene, butyl hydroxyl anisole, a gallic acid ester, etc.

The antioxidant aiding agent may be, for example, phosphate, citric acid, ascorbic acid, maleic acid, malonic acid, succinic acid, fumaric acid, cephalin, hexameta phosphate, phytic acid, ethylene diamine tetraacetic acid, etc.

Other components to be blended may be, for example, an antiseptic agent (for example, methyl paraben, ethyl paraben, butyl paraben, phenoxy ethanol, etc.); an antiphlogistic agent (for example, a glycyrrhizic acid derivative, a glycyrrhetinic acid derivative, thiotaurine, hypotaurine, Japanese cypress thiol, zinc oxide, allantoin, etc.), a skin whitening agent (for example, strawberry saxifrage extract, arbutin, tranexamic acid, L-ascorbic acid, magnesium salt of L-ascorbic acid phosphate ester, L-ascorbic acid glucoside, potassium 4-methoxy salicylate, etc.); various types of extracts (for example, cork, Japanese goldthread, princess flower, peony, swertia herb, birch, sage, loquat, carrot, aloe, cheeses, iris, grape, coix seed, loofah, lily, saffron, rhizoma, shrews, St. John's wort, restharrow, garlic, red pepper, sun dried tangerine peel, angelica, seaweed, etc.), an activator (for example, royal jelly, a photosensitizer, a cholesterol derivative, etc.); blood circulation promoters; etc.

In the transparent solid cosmetic of the present disclosure, it is possible to blend an oil based gelling agent component such as dextrin palmitate, glyceryl behenate eicosane diacid, polyamide-3, polyamide-8, 2-ethylhexanoyl glutamate butyl amide, N-2-ethylhexanoyl-L-glutamate dibutyl amide, etc., as a solidifying aiding agent within a range that will maintain the transparency of the cosmetic.

The transparent solid cosmetic of the present disclosure is prepared as a gel or a solid. The format of the cosmetic product is not particularly limited, and may be, for example, a makeup cosmetic such as a foundation, a rouge, a lip gloss, a lip cream, an eye shadow, etc., a cosmetic base, a sunscreen, a skin care cosmetic, a hair stick, a body cosmetic, an antiperspirant cosmetic, and a hair cosmetic such as pomade, etc. The transparent solid cosmetic of the present disclosure may be favorably utilized by being filled in a container or as a transparent solid cosmetic in the form of a stick.

The transparent solid composition of the present disclosure and the cosmetic that employs the transparent solid composition may be prepared by a conventional method. For example, the cosmetic may be prepared by melting and dispersing the components described above at a temperature within a range from 70 to 100° C., pouring the melted mixture into a desired die or container, and then cooling to solidify the mixture.

EXAMPLES

Hereinafter, the present disclosure will be described in greater detail with reference to Examples. However, the present disclosure is not limited to these Examples. The content of each component which is blended is indicated as % by mass, unless otherwise particularly noted.

Note that the Examples and Comparative Examples are produced by conventional methods. Specifically, a solidifying agent (12-hydroxystearic acid, dextrin fatty acid ester, etc.) is added to an oil component, then melted by being heated to a temperature within a range from 80° C. to 90° C. Thereafter, the remaining components (ultraviolet ray absorbing agent, powder, etc.) are added and dispersed by a homomixer until uniformly dispersed. The mixture is deaerated and then solidified at room temperature, to obtain various samples.

[Refractive Index]

Refractive indices were measured at a temperature of 25° C., employing an AUTOMATIC REFRACTOMETER by Rudolph Research Analytical.

[Transparency]

Samples were poured into transparent resin containers such that the thicknesses thereof became 10 mm. A panel of experts evaluated the clarity of text placed under the containers written in Times New Roman font with a font size of 88, at a temperature of 25° C.

5: Text was extremely clearly visible, and the clarity is extremely high.
4: Text was clearly visible, and the clarity is high.
3: Text is visible, but clarity is somewhat low.
2: Text is barely visible, and clarity is low.
1: Text is not visible, and the sample is opaque.

[Stability]

After filling containers with each sample, the containers were left static in temperature controlled tanks at −5° C., room temperature, and 37° C. The state of the outer appearance was evaluated each week during the month.

Stable: No changes in outer appearance occurred at any of the temperatures, and stability is superior.
Unstable: Changes such as oil flooding, etc. are observed at one or more temperatures.

(1) Consideration of Solidifying Agent

Solid compositions having various refractive indices were produced with the compositions shown in Table 1, employing 12-hydroxystearic acid or dextrin palmitate as a solidifying agent, or without employing a solidifying agent, and then the transparency and stability of the solid compositions were evaluated.

As shown in Table 1, Examples 1 through 5, in which 12-hydroxyl stearic acid was employed as the solidifying agent, a high refractive index oil component and a low refractive index oil component were blended such that the refractive index of the composition as a whole is within a range from 1.47 to 1.55 exhibited high transparency even if ultraviolet ray absorbing agents were blended at 10% by mass, and also had superior stability. Meanwhile, in cases that dextrin palmitate was employed as the solidifying agent, cloudiness was generated and a transparent solid composition could not be produced (Comparative Examples 3 and 4).

TABLE 1

|  | Ingredients | Example 1 | Example 2 | Example 3 | Example 4 | Example 5 | Comparative Example 1 | Comparative Example 2 |
|---|---|---|---|---|---|---|---|---|
| Solidifying Agent | 12-hydroxy stearic acid | 2.5 | 5 | 10 | 2.5 | 2.5 | 5 | 5 |
|  | Dextrin palmitate (*1) |  |  |  |  |  |  |  |
| Oil Component | Trimethyl pentaphenyl polysiloxane (*2) [Refractive Index: 1.58] | 27 | 27 | 27 | 43.75 | 43.75 |  | 55 |
|  | Isododecane [Refractive Index 1.42] (Volatile) | 28 | 28 | 28 | 43.75 | 43.75 | 27.5 |  |
|  | Dimethyl polysiloxane (*3) [Refractive Index: 1.38] (Volatile) |  |  |  |  |  | 27.5 |  |
| UV Ray Absorbing Agent | t-butyl methoxy dibenzoyl methane (*4) | 3 | 3 | 3 | 3 | 3 | 3 | 3 |
|  | Ethylhexyl methoxy cinnamate (*5) | 7 | 7 | 7 | 7 | 7 | 7 | 7 |
| Powder | (HDI/trimethyrolhexyl lactone) cross polymer (*6) [Refractive Index: about 1.5] | 32.5 | 30 | 25 |  |  | 30 | 30 |
| Evaluations | Total | 100 | 100 | 100 | 100 | 100 | 100 | 100 |
|  | Refractive Index (n) | 1.51 | 1.51 | 1.51 | 1.51 | 1.51 | 1.42 | 1.58 |
|  | Transparency (thickness: 10 mm) | 4 | 4 | 4 | 5 | 5 | 1 | 1 |
|  | Stability | Stable | Stable | Stable | Stable | Stable | Stable | Stable |

|  | Ingredients | Comparative Example 3 | Comparative Example 4 | Comparative Example 5 | Comparative Example 6 | Comparative Example 7 | Comparative Example 8 |
|---|---|---|---|---|---|---|---|
| Solidifying Agent | 12-hydroxy stearic acid |  |  | 5 | 5 | 0.8 | 16 |
|  | Dextrin palmitate (*1) | 5 | 5 |  |  |  |  |
| Oil Component | Trimethyl pentaphenyl polysiloxane (*2) [Refractive Index: 1.58] | 27 | 30 |  | 85 | 30 | 30 |
|  | Isododecane [Refractive Index 1.42] (Volatile) | 28 |  | 42.5 |  | 25 | 25 |
|  | Dimethyl polysiloxane (*3) [Refractive Index: 1.38] (Volatile) |  | 25 | 42.5 |  |  |  |
| UV Ray Absorbing Agent | t-butyl methoxy dibenzoyl methane (*4) | 3 | 3 | 3 | 3 | 3 | 3 |
|  | Ethylhexyl methoxy cinnamate (*5) | 7 | 7 | 7 | 7 | 7 | 7 |
| Powder | (HDI/trimethyrolhexyl lactone) cross polymer (*6) [Refractive Index: about 1.5] | 30 | 30 |  |  | 34.2 | 19 |
| Evaluations | Total | 100 | 100 | 100 | 100 | 100 | 100 |
|  | Refractive Index (n) | 1.51 | 1.51 | 1.42 | 1.58 | 1.51 | 1.51 |
|  | Transparency (thickness: 10 mm) | 1 | 1 | 1 | 1 | 3 | 5 |
|  | Stability | Stable | Stable | Stable | Stable | UnStable | UnStable |

(*1): Rheopearl KL2 (by Chiba Flour Milling)
(*2): PH-1555HRIC (by Toray/Dow Corning)
(*3): KF-96-1.5CS (by Shin Etsu Chemical Industries)
(*4): Parsol 1789 (by DSM Nutrition Japan)
(*5): Parsol MCX (by DSM DSM Nutrition Japan)
(*6): Plastic Powder D400 (by Toshiki Pigment)

In addition, Comparative Examples 1 and 5, in which the refractive indices of the compositions were less than 1.47, as well as Comparative Examples 2 and 6, in which the refractive indices were greater than 1.55, exhibited low transparency. Comparative Example 7, in which the content of 12-hydroxyl stearic acid was less than 1%, had insufficient solidifying strength and insufficient stability. In addition, Comparative Example 8, in which the content of 12-hydroxystearic acid was 15% or greater, had an excessive amount of the solidifying agent with respect to the preparation, which caused precipitation of 12-hydroxystearic acid, and stability was insufficient.

Note that although the results are not shown, evaluations were conducted regarding stickiness and a skin unevenness correcting effect when applied for the above compositions. Examples 1 through 3, which include a powder along with a volatile oil component, had less stickiness and a superior sensation of use compared to Examples 4 and 5 that do not include a powder, and also exhibited a skin unevenness correcting effect when applied to the skin.

(2) Consideration of Ultraviolet ray Absorbing Agent

Solid compositions having refractive indices of approximately 1.5 were produced by blending the ultraviolet ray absorbing agents of the compositions shown in Table 2, and then the transparency and stability of the solid compositions were evaluated.

TABLE 2

|   | Ingredients | Example 6 | Example 7 | Example 8 | Example 9 | Example 10 | Example 11 | Example 12 | Example 13 |
|---|---|---|---|---|---|---|---|---|---|
| Solidifying Agent | 12-hydroxy stearic acid | 5 | 5 | 5 | 5 | 5 | 5 | 5 | 5 |
| Oil Component | Trimethyl pentaphenyl polysiloxane [Refractive Index: 1.58] (*2) | 22 | 22 | 22 | 22 | 22 | 22 | 22 | 22 |
|   | Isododecane[Refractive Index: 1.42] (Volatile) | 20 | 20 | 20 | 20 | 20 | 20 | 20 | 20 |
|   | Isohexadecane[Refractive Index: 1.43] (Volatile) | 8 | 8 | 8 | 8 | 8 | 8 | 8 | 8 |
| UV Ray Absorbing Agent | t-butyl methoxy dibenzoyl methane (*4) | 10 |   |   |   |   |   | 3 | 3 |
|   | Octocrylene (*7) |   | 10 |   |   |   |   |   | 2.5 |
|   | 2-hydroxy 4-methoxybenzophenone (*8) |   |   | 10 |   |   |   |   | 5 |
|   | Homomentyl salicylate (*9) |   |   |   | 10 |   |   |   | 20 |
|   | Octyl salicylate (*10) |   |   |   |   | 10 |   |   |   |
|   | Ethylhexyl methoxy cinnamate (*5) |   |   |   |   |   | 10 | 7 |   |
| Powder | (HDI/trimethyrolhexyl lactone) cross polymer (*6) [Refractive Index about 1.5] | 35 | 35 | 35 | 35 | 35 | 35 | 35 | 14.5 |
|   | Total | 100 | 100 | 100 | 100 | 100 | 100 | 100 | 100 |
| Evaluations | Refractive Index (n) | 1.51 | 1.51 | 1.51 | 1.51 | 1.51 | 1.51 | 1.51 | 1.51 |
|   | Transparency (thickness: 10 mm) | 4 | 4 | 4 | 4 | 4 | 4 | 4 | 5 |
|   | Stability | Stable | Stable | Stable | Stable | Stable | Stable | Stable | Stable |

(*7): Uvinul N539T (by BASF)
(*8): Uvinul M40 (by BASF)
(*9): Neo Heliopan HMS (by Symrise)
(*10): Neo Heliopan OS (by Symrise)

The present disclosure was capable of preparing transparent solid compositions having high transparency and superior stability, by blending each type of the ultraviolet ray absorbing agents in amounts of 5% by mass or greater.

(3) Consideration of Oil Component

Solid compositions having refractive indices of approximately 1.5 were produced by blending the oil components with the compositions shown in Table 3, and then the transparency and stability of the solid compositions were evaluated.

TABLE 3

|   | Ingredients | Example 14 | Example 15 | Example 16 | Example 17 | Example 18 | Example 19 |
|---|---|---|---|---|---|---|---|
| Solidifying Agent | 12-hydroxy stearic acid | 5 | 5 | 5 | 5 | 5 | 5 |
| Oil Component | Trimethyl pentaphenyl polysiloxane (*2) [Refractive Index: 1.58] | 22 | 21 | 33 | 27 | 26 |   |
|   | Diphenyl dimethicone (*11) [Refractive Index: 1.505] |   |   |   |   |   | 34 |
|   | Triethylhexanoin (*12) [Refractive Index 1.446] | 33 |   |   |   |   |   |
|   | Tri (caprylic acid/capric acid) glyceryl (*13) [Refractive Index 1.45] |   |   | 34 |   |   |   |
|   | Dimethyl polysiloxane (*3) [Refractive Index 1.38] (Volatile) |   |   |   | 22 |   |   |
|   | Isododecane [Refractive Index 1.42] (Volatile) |   |   |   |   | 28 | 21 |
|   | Isohexadecane [Refractive Index 1.44] (Volatile) |   |   |   |   |   | 8 |
|   | (Hydrogenated rosin/diisostearic acid) glyceryl (*14) |   |   |   |   |   | 30 |

TABLE 3-continued

|  | Ingredients | Example 14 | Example 15 | Example 16 | Example 17 | Example 18 | Example 19 |
|---|---|---|---|---|---|---|---|
| UV Ray Absorbing Agent | t-butyl methoxy dibenzoyl methane (*4) | 3 | 3 | 3 | 3 | 3 | 3 |
|  | Ethylhexyl methoxy cinnamate (*5) | 7 | 7 | 7 | 7 | 7 | 7 |
| Powder | (HDI/trimethyrolhexyl lactone) cross polymer (*5) [Refractive Index about 1.50] | 30 | 30 | 30 | 30 | 30 | 21 |
|  | Total | 100 | 100 | 100 | 100 | 100 | 100 |
| Evaluations | Refractive Index (n) | 1.51 | 1.51 | 1.51 | 1.51 | 1.51 | 1.5 |
|  | Transparency (thickness: 10 mm) | 4 | 4 | 4 | 4 | 4 | 4 |
|  | Stability | Stable | Stable | Stable | Stable | Stable | Stable |

(*11): KF-54 (by Shin Etsu Chemical Industries)
(*12): RA-G-308 (by Nippon Fine Chemical)
(*13): O.D.O (by Nisshin Oillio)
(*14): RIG-12V (by Nippon Fine Chemical)

By blending oils, each type of which has a refractive index within a range from 1.5 through 1.7, and oils having a refractive index of 1.3 or greater and less than 1.5 to set the refractive index of the composition as a whole to be within a range from 1.47 to 1.55, it was possible to prepare transparent solid compositions that have high transparency and superior stability even if significant amounts of ultraviolet ray absorbing agents are blended. Examples 16 through 18 had high transparency even if a volatile silicone oil or a volatile hydrocarbon oil was blended, and were had superior stability.

(4) Consideration of Refractive Index

Solid compositions having various refractive indices were produced with the compositions shown in Table 4, and then the transparency and stability thereof were evaluated. Note that FIG. 1 is a photograph of the evaluation of transparency. In addition, FIG. 2 illustrates the results of evaluations of L values which were conducted for Examples 21 through 26 employing a color difference meter (Spectrophotometer SE7700 by Nippon Denshoku Industries) with a table, a graph, and photographs.

TABLE 4

|  | Ingredients | Comparative Example 9 | Example 20 | Example 21 | Example 22 | Example 23 | Example 24 |
|---|---|---|---|---|---|---|---|
| Solidifying Agent | 12-hydroxy stearic acid | 2.5 | 2.5 | 2.5 | 2.5 | 2.5 | 2.5 |
| Oil Component | Trimethyl pentaphenyl polysiloxane (*2) [Refractive Index: 1.58] |  |  | 3.1 | 10.4 | 17.7 | 25 |
|  | Tri (caprylic acid/capric acid) glyceryl (*13) [Refractive Index: 1.45] | 82 | 72.7 | 63.4 | 56.1 | 48.8 | 41.5 |
| UV Ray Absorbing Agent | t-butyl methoxy dibenzoyl methane (*4) | 1.5 | 2.4 | 3 | 3 | 3 | 3 |
|  | Ethylhexyl methoxy cinnamate (*5) | 3.75 | 6 | 7.5 | 7.5 | 7.5 | 7.5 |
|  | Homomentyl salicylate (*9) | 5 | 8 | 10 | 10 | 10 | 10 |
|  | Octocrylene (*7) | 1.25 | 2 | 2.5 | 2.5 | 2.5 | 2.5 |
|  | 2-hydroxy 4-methoxy benzophenone (*8) | 1.5 | 2.4 | 3 | 3 | 3 | 3 |
|  | Octyl salicylate (*10) | 2.5 | 4 | 5 | 5 | 5 | 5 |
|  | Total | 100 | 100 | 100 | 100 | 100 | 100 |
| Evaluations | Refractive Index (n) | 1.46 | 1.47 | 1.48 | 1.49 | 1.5 | 1.51 |
|  | Transparency (thickness: 10 mm) | 3 | 4 | 4 | 5 | 5 | 5 |
|  | Stability | Stable | Stable | Stable | Stable | Stable | Stable |

|  | Ingredients | Example 25 | Example 26 | Example 27 | Example 28 | Comparative Example 10 |
|---|---|---|---|---|---|---|
| Solidifying Agent | 12-hydroxy stearic acid | 2.5 | 2.5 | 2.5 | 2.5 | 2.5 |
| Oil Component | Trimethyl pentaphenyl polysiloxane (*2) [Refractive Index: 1.58] | 32.2 | 39.5 | 46.5 | 54.5 | 61.5 |
|  | Tri (caprylic acid/capric acid) glyceryl (*13) [Refractive Index: 1.45] | 34.3 | 27 | 20 | 12 | 5 |
| UV Ray Absorbing Agent | t-butyl methoxy dibenzoyl methane (*4) | 3 | 3 | 3 | 3 | 3 |
|  | Ethylhexyl methoxy cinnamate (*5) | 7.5 | 7.5 | 7.5 | 7.5 | 7.5 |
|  | Homomentyl salicylate (*9) | 10 | 10 | 10 | 10 | 10 |
|  | Octocrylene (*7) | 2.5 | 2.5 | 2.5 | 2.5 | 2.5 |
|  | 2-hydroxy 4-methoxy benzophenone (*8) | 3 | 3 | 3 | 3 | 3 |
|  | Octyl salicylate (*10) | 5 | 5 | 5 | 5 | 5 |
|  | Total | 100 | 100 | 100 | 100 | 100 |
| Evaluations | Refractive Index (n) | 1.52 | 1.53 | 1.54 | 1.55 | 1.56 |
|  | Transparency (thickness: 10 mm) | 5 | 5 | 4 | 4 | 3 |
|  | Stability | Stable | Stable | Stable | Stable | Stable |

TABLE 5

| | Ingredient | Example 29 | Example 30 |
|---|---|---|---|
| Solidifying Agent | 12-hydroxystearic acid | 5 | 5 |
| | Dibutyl lauroyl glutamide | 0.67 | |
| | Dibutyl ethylhexanoyl glutamide | | 0.67 |
| | Polyamide-8 | 0.5 | |
| | Polyamide-3 | | 0.5 |
| Oil | Trimethyl pentaphenyl polysiloxane | 23.7 | 23.7 |
| | Tri (caprylic acid/capric acid) glyceryl | 39.13 | 39.13 |
| UV Ray Absorbing Agent | t-butyl methoxy benzoyl methane | 3 | 3 |
| | Ethylhexyl methoxy cinnamate | 5 | 5 |
| | Homomentyl salicylate (homosalate) | 10 | 10 |
| | Octocrylene | 2 | 2 |
| | 2-hydroxy 4-benzophenone | 3 | 3 |
| | Hexyl diethyl amino hydroxybenzoyl benzoate | 2 | 2 |
| | Bisethyl hexyl oxyphenol methoxy phenyl triazine | 0.5 | 0.5 |
| | 2,4,6-trianilino-p-(carbo-2'-ethylhexyl-1'-oxy)-1,3,5-triazine | 0.5 | 0.5 |
| | Homosalate | 5 | 5 |
| | Total | 100 | 100 |
| Evaluations | Refractive Index | 1.51 | 1.51 |
| | Transparency (10 mm Thickness) | 5 | 5 |
| | Stability | Stable | Stable |

As is clear from Table 4, Table 5, and FIG. 1, high transparency was exhibited by samples having refractive indices within a range from 1.47 to 1.55 (Examples 20 through 28). Particularly, Examples 22 through 26, which had refractive indices within a range from 1.49 to 1.53, exhibited even higher transparency. In contrast, in the case that the refractive index was less than 1.47 (Comparative Example 9) or greater than 1.55 (Comparative Example 10), transparency deteriorated significantly. The relationship between refractive indices and L values shown in FIG. 2 supports the fact that the maximum L value, which represents the highest transparency, is exhibited when the refractive index is 1.51. In addition, it is possible to combine a polyamide series solidifying agent as an oil phase solidifying aiding agent within a range that maintains the transparency of the cosmetic (Examples 29 and 30).

The transparent solid cosmetics below were produced by conventional methods.

Preparation Example 1

Cosmetic Base 12-hydroxystearic acid: 5
Trimethyl pentaphenyl polysiloxane (*2): 26
Isododecane: 21
Isohexadecane: 8
t-butyl methoxy dibenzoyl methane (*4) 3
Ethylhexyl methoxy cinnamate (*5): 7
(HDI/trimethyrolhexyl lactone) cross polymer: (*6): 29.9
Red dye: 0.1
Total: 100

Preparation Example 2

Skin Care Cosmetic 12-hydroxystearic acid: 5
Trimethyl pentaphenyl polysiloxane (*2): 21
Tri (caprylic acid/capric acid) glyceryl (*13): 34
t-butyl methoxy dibenzoyl methane (*4) 3
Ethylhexyl methoxy cinnamate (*5): 7
(HDI/trimethyrolhexyl lactone) cross polymer: (*6): 29.9
Photoluminescent inorganic pigment (MetaShine 1040RS): 0.1
Total: 100

Preparation Example 3

Part Specific Foundation 12-hydroxystearic acid: 2.5
Dextrin palmitate: 0.1
Trimethyl pentaphenyl polysiloxane (*2): 21
Tri (caprylic acid/capric acid) glyceryl (*13): 34
t-butyl methoxy dibenzoyl methane (*4) 3
Ethylhexyl methoxy cinnamate (*5): 7.5
(HDI/trimethyrolhexyl lactone) cross polymer: (*6): 15.0
Silicate anhydride: 10
Nylon: remainder
Total: 100

Preparation Example 4

Lip Gloss 12-hydroxystearic acid: 5
Glyceryl behenate eicosane diacid: 0.1
Trimethyl pentaphenyl polysiloxane (*2): 21
Tri (caprylic acid/capric acid) glyceryl (*13): 34
t-butyl methoxy dibenzoyl methane (*4) 3
Ethylhexyl methoxy cinnamate (*5): 7
(HDI/trimethyrolhexyl lactone) cross polymer (*6): 29.8
Red dye: 0.1
Total: 100

Preparation 5

Sunscreen 12-hydroxystearic acid: 5
Polyamide-3: 0.1
Polyamide-8: 0.1
Trimethyl pentaphenyl polysiloxane (*2): 26
Isododecane: 21
Isohexadecane: 8
t-butyl methoxy dibenzoyl methane (*4) 3
Ethylhexyl methoxy cinnamate (*5): 10
2, 4, 6-trianilino-p-(carbo-2'-ethylhexyl-1'-oxy)-1, 3, 5-triazine: 1
{2-[4-(diethyl amino)-2-hydroxybenzoyl]} benzoate hexyl ester: 1
2, 4-bis-[{4-(2-ethylhexyloxy)-2-hydroxy}-phenyl]-6-(4-methoxy phenyl)-1, 3, 5-triazine: 1
(HDI/trimethyrolhexyl lactone) cross polymer (*6): 23.8
Total: 100

Preparation 6

Sunscreen 12-hydroxystearic acid: 5
2-ethylhexanoyl glutamate butyl amide: 0.1
N-2-ethyihexanoyl-L-glutamate dibutyl amide: 0.1
Trimethyl pentaphenyl polysiloxane (*2): 28
Isododecane: 22

Isohexadecane: 8
t-butyl methoxy dibenzoyl methane (*4) 3
Ethylhexyl methoxy cinnamate (*5): 10
2, 4, 6-trianilino-p-(carbo-2'-ethylhexyl-1'-oxy)-1, 3, 5-triazine: 1
{2-[4-(diethyl amino)-2-hydroxybenzoyl]} benzoate hexyl ester: 1
2, 4-bis-[{4-(2-ethylhexyloxy)-2-hydroxy}-phenyl]-6-(4-methoxy phenyl)-1, 3, 5-triazine: 1
(HDI/trimethyrolhexyl lactone) cross polymer (*6): 20.8
Total: 100

Preparation 7

Body Cosmetic 12-hydroxystearic acid: 5
Trimethyl pentaphenyl polysiloxane (*2): 21
Tri (caprylic acid/capric acid) glyceryl (*13): 34
t-butyl methoxy dibenzoyl methane (*4) 3
Ethylhexyl methoxy cinnamate (*5): 7
(HDI/trimethyrolhexyl lactone) cross polymer (*6): 24.9
Nylon-12: 1
Polyethylene: 1
Polyurethane: 1
Silica: 2
Fragrance: 0.1
Total: 100

Preparation 8

Sunscreen 12-hydroxystearic acid: 7.5
Polyamide-8: 1.5
Dibutyl lauroyl glutamide: 2
Diphenyl siloxy phenyl trimethicone: 30
Triethyl hexanoin: 16.5
Mineral oil: 10
PPG-17: 1
Homosalate: 10
Octyl salicylate: 5
Octocrylene: 5
Oxybenzone-3: 5
t-butyl methoxy dibenzoyl methane (*4): 2.5
Ethylhexyl methoxy cinnamate (*5): 5
Hydrophobized silica: 1
Fragrance: q. s.
Total: 100

The transparent cosmetics of the above preparations exhibited superior transparency in the outer appearance of the base materials thereof (the evaluations by the transparency test described above were all "5"), and are transparent cosmetics having favorable sensations of use, which are also stable.

The invention claimed is:
1. A transparent solid composition, comprising
   (a) 12-hydroxystearic acid in an amount within a range from 1 to 15% by mass;
   (b) an oil having a refractive index within a range from 1.5 to 1.7 in an amount within a range from 3.1 to 54.5% by mass;
   (c) an oil having a refractive index of 1.3 or greater and less than 1.5 in an amount within a range from 5 to 63.4% by mass; and
   (d) one type or two or more types of an ultraviolet ray absorbing agent in an amount within a range from 5 to 50% by mass;
   the refractive index of the transparent solid composition being within a range from 1.47 to 1.55.
2. A transparent solid composition as defined in claim 1, wherein:
   the ultraviolet ray absorbing agent is selected from the group consisting of t-butyl methoxy dibenzoyl methane, ethylhexyl methoxy cinnamate, homomentyl salicylate (homosalate), octyl salicylate, octocrylene, 2-hydroxy 4-methoxybenzophenone, hexyl diethyl amino hydroxybenzoyl benzoate, bis ethylhexyl oxyphenol methoxy phenyl triazine, and 2, 4, 6-trianilino-p-(carbo-2'-ethylhexyl-1'-oxy)-1, 3, 5-triazine.
3. A transparent solid composition as defined in claim 1, further comprising:
   a powder having a refractive index within a range from 1.45 to 1.55.
4. A transparent solid composition as defined in claim 1, wherein:
   the (c) oil having a refractive index of 1.3 or greater and less than 1.5 includes a volatile oil.
5. A transparent solid composition as defined in claim 4, wherein
   the (c) oil having a refractive index of 1.3 or greater and less than 1.5 includes a hydrocarbon series volatile oil.
6. A transparent solid composition as defined in claim 1, wherein:
   the transparent solid composition is in the form of a stick.
7. A transparent solid cosmetic comprising a transparent solid composition as defined in claim 1 as a base material.
8. A transparent solid oil composition as defined in claim 1, further comprising:
   an oil solidifying agent selected from the group consisting of dibutyl lauroyl glutamide, dibutyl ethylhexanoyl glutamide, polyamide-3, and polyamide-8.
9. A transparent solid composition as defined in claim 2, further comprising:
   a powder having a refractive index within a range from 1.45 to 1.55.
10. A transparent solid composition as defined in claim 2, wherein:
    the (c) oil having a refractive index of 1.3 or greater and less than 1.5 includes a volatile oil.
11. A transparent solid composition as defined in claim 3, wherein:
    the (c) oil having a refractive index of 1.3 or greater and less than 1.5 includes a volatile oil.
12. A transparent solid composition as defined in claim 4, wherein
    the (c) oil having a refractive index of 1.3 or greater and less than 1.5 includes a hydrocarbon series volatile oil.
13. A transparent solid composition as defined in claim 2, wherein:
    the transparent solid composition is in the form of a stick.
14. A transparent solid composition as defined in claim 3, wherein:
    the transparent solid composition is in the form of a stick.
15. A transparent solid composition as defined in claim 4, wherein:
    the transparent solid composition is in the form of a stick.
16. A transparent solid composition as defined in claim 5, wherein:
    the transparent solid composition is in the form of a stick.
17. A transparent solid oil composition as defined in claim 2, further comprising:

an oil solidifying agent selected from the group consisting of dibutyl lauroyl glutamide, dibutyl ethylhexanoyl glutamide, polyamide-3, and polyamide-8.

18. A transparent solid oil composition as defined in claim 3, further comprising:
an oil solidifying agent selected from the group consisting of dibutyl lauroyl glutamide, dibutyl ethylhexanoyl glutamide, polyamide-3, and polyamide-8.

19. A transparent solid oil composition as defined in claim 4, further comprising:
an oil solidifying agent selected from the group consisting of dibutyl lauroyl glutamide, dibutyl ethylhexanoyl glutamide, polyamide-3, and polyamide-8.

20. A transparent solid oil composition as defined in claim 6, further comprising:
an oil solidifying agent selected from the group consisting of dibutyl lauroyl glutamide, dibutyl ethylhexanoyl glutamide, polyamide-3, and polyamide-8.

* * * * *